United States Patent [19]

Duffett

[11] Patent Number: Plant 6,058

[45] Date of Patent: Dec. 8, 1987

[54] CHRYSANTHEMUM PLANT NAMED SOLO

[75] Inventor: William E. Duffett, Salinas, Calif.

[73] Assignee: Yoder Brothers, Inc., Barberton, Ohio

[21] Appl. No.: 786,003

[22] Filed: Oct. 10, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Solo particularly characterized as to uniqueness by the combined characteristics of flat capitulum form; daisy capitulum type; white ray floret color; diameter across face of capitulum ranging from 5 to 6 cm. at maturity; uniform seven week photoperiodic flowering response to short days; medium plant height when grown as a pinched spray pot mum; spreading branching pattern; tolerance of both low winter 12° C. to 14° C. and high summer 23° C. to 38° C. temperatures for bud initiation and flower development; and golden yellow, pollen-producing disc florets.

3 Drawing Figures

The present invention comprises a new and distinct cultivar of Chrysanthemum, botanically known as *Dentrenthema morifolium*, Ramat., previously *Chrysanthemum morifolium*, Ramat., named Solo.

Solo is a product of a planned breeding program which had the objective of creating new Chrysanthemum cultivars for pinched spray pot mum programs having daisy capitulum type, white ray floret color, eight week flowering response and the ability to produce commercially acceptable quality in year around programs. Such traits in combination were not present or required improvements in previously available commercial cultivars.

Solo, identified as 82005018, was originated from a cross made in a controlled breeding program in Salinas, Calif. in 1981. The female parent, identified as 79F54008, was the progeny of Pert, disclosed in U.S. Plant Pat. No. 4,764, as female parent and an unnamed seedling as male parent, both originated by the present inventor. The male parent of Solo, identified as 79P73001, was originated from a cross between two unnamed seedlings.

Solo was discovered and selected as one flowering plant within the progeny of the stated cross by William E. Duffett in September of 1982 in a controlled environment in Salinas, Calif.

The first act of asexual reproduction of Solo was accomplished when vegetative cuttings were taken from the initial selection in December of 1982 in a controlled environment in Salinas, Calif. by a technician working under formulations established and supervised by William E. Duffett. Horticultural examination of selected units initiated April 1983 has demonstrated that the combination of characteristics as herein disclosed for Solo are firmly fixed and are retained through successive generations of asexual reproduction.

Solo has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Solo which in combination distinguish this Chrysanthemum as a new and distinct cultivar:

(1) Flat capitulum form.
(2) Daisy capitulum type.
(3) White ray floret color.
(4) Diameter across face of capitulum ranging from 5 to 6 cm. at maturity.
(5) Uniform seven week photoperiodic flowering response to short days.
(6) Medium plant height, requiring 2 long day weeks prior to pinch and short days, and 1–2 applications of 2500 ppm B-9 SP, the first at 14, the second at 21 days after the beginning of short days to attain a flowered plant height of 25 to 35 cm. in 6" pots.
(7) Spreading branching pattern.
(8) Tolerance of low winter 12° C. to 14° C. temperatures.
(9) Tolerance of high summer 23° C. to 38° C. temperatures.
(10) Golden yellow pollen-producing disc florets.

The accompanying photographic drawings depict typical leaf and inflorescence characteristics of Solo.

Sheet 1 is a color photograph of a plant of Solo grown as a pinched, spray pot mum, with colors being as accurate as possible with renditions of this type.

Sheet 2 is a black and white photograph of three views of the inflorescence of Solo.

Sheet 3 shows the upper and under surface of the leaves of Solo in three stages of growth (mature, intermediate and immature).

Of the many commercial cultivars known to the present inventor the most similar in comparison to Solo is Garland, disclosed in U.S. Plant Pat. No. 3,576. Reference is made to attached Chart A which compares certain characteristics of Solo to those same characteristics of Garland. Similar traits are type, form and color. Solo has lighter and smaller foliage, shorter, more spreading plant habit, more abundant pollen production, faster response time, smaller capitulum diameter, shorter ray floret length, and its tolerance of both high and low temperatures results in more rapid response and shorter crop time.

In the following description, color references are made to The Royal Horticultural Society Colour Chart. The color values were determined between 3:00 and 3:15 p.m. on Nov. 27, 1984 under 380 foot-candle light intensity at Salinas, Calif.

Classification:

*Botanical.*—*Dentrenthema morifolium,* Ramat., cv Solo.

*Commercial.*—Daisy spray pot mum.

INFLORESCENCE

A. Capitulum:

*Form.*—Flat.

*Type.*—Daisy.

*Diameter across face.*—5 to 6 cm.

B. Corolla of ray florets:

*Color (general tonality from a distance of three meters).*—White.

*Color (upper surface).*—155B.

*Color (under surface).*—155B.

Shape.—Short, broad, with rounded tip.

C. Corolla of disc florets:

*Color (mature).*—14B.

*Color (immature).*—154A.

D. Reproductive organs:

*Androecium.*—Present disc florets only; abundant pollen.

*Gynoecium.*—Present both ray and disc florets.

PLANT

A. General appearance:

*Height.*—Medium.

*Branching pattern.*—Spreading.

B. Foliage:

*Color (upper surface).*—138A.

*Color (under surface).*—138B.

*Shape.*—Moderately lobed. Small with broadly dented serration.

CHART A

COMPARISON OF SOLO AND GARLAND

| CULTIVAR | RAY FLORET COLOR | CAPITULUM FORM AND TYPE | BRANCHING PATTERN |
|---|---|---|---|
| SOLO | WHITE | FLAT DAISY | SPREADING |
| GARLAND | WHITE | FLAT DAISY | SEMI UPRIGHT |

| CULTIVAR | DIAMETER ACROSS FACE OF CAPITULUM | PLANT HEIGHT | FLOWERING RESPONSE PERIOD | TEMPERATURE TOLERANCE |
|---|---|---|---|---|
| SOLO | 5 to 6 cm. | MEDIUM | SEVEN WEEKS | LOW: 12° C. to 14° C. HIGH: 23° C. to 38° C. |
| GARLAND | 7 to 9 cm. | TALL | NINE WEEKS | LOW: 13° C. to 14° C. HIGH: 18° C. to 22° C. |

COMPARISONS MADE OF PLANTS GROWN AS PINCHED, SPRAY POT MUMS IN SALINAS, CALIFORNIA AND LEAMINGTON, ONTARIO, CANADA

I claim:

1. A new and distinct cultivar of *Dentrenthema morifolium,* Ramat., named Solo, as described and illustrated, and particularly characterized as to uniqueness by the combined characteristics of flat capitulum form; daisy capitulum type; white ray floret color; diameter across face of capitulum ranging from 5 to 6 cm. at maturity; uniform seven week flowering response; medium plant height; spreading branching pattern; tolerance of both low winter 12° C. to 14° C. and high summer 23° C. to 38° C. temperatures for bud initiation and flower development; and golden yellow pollen-producing disc florets.

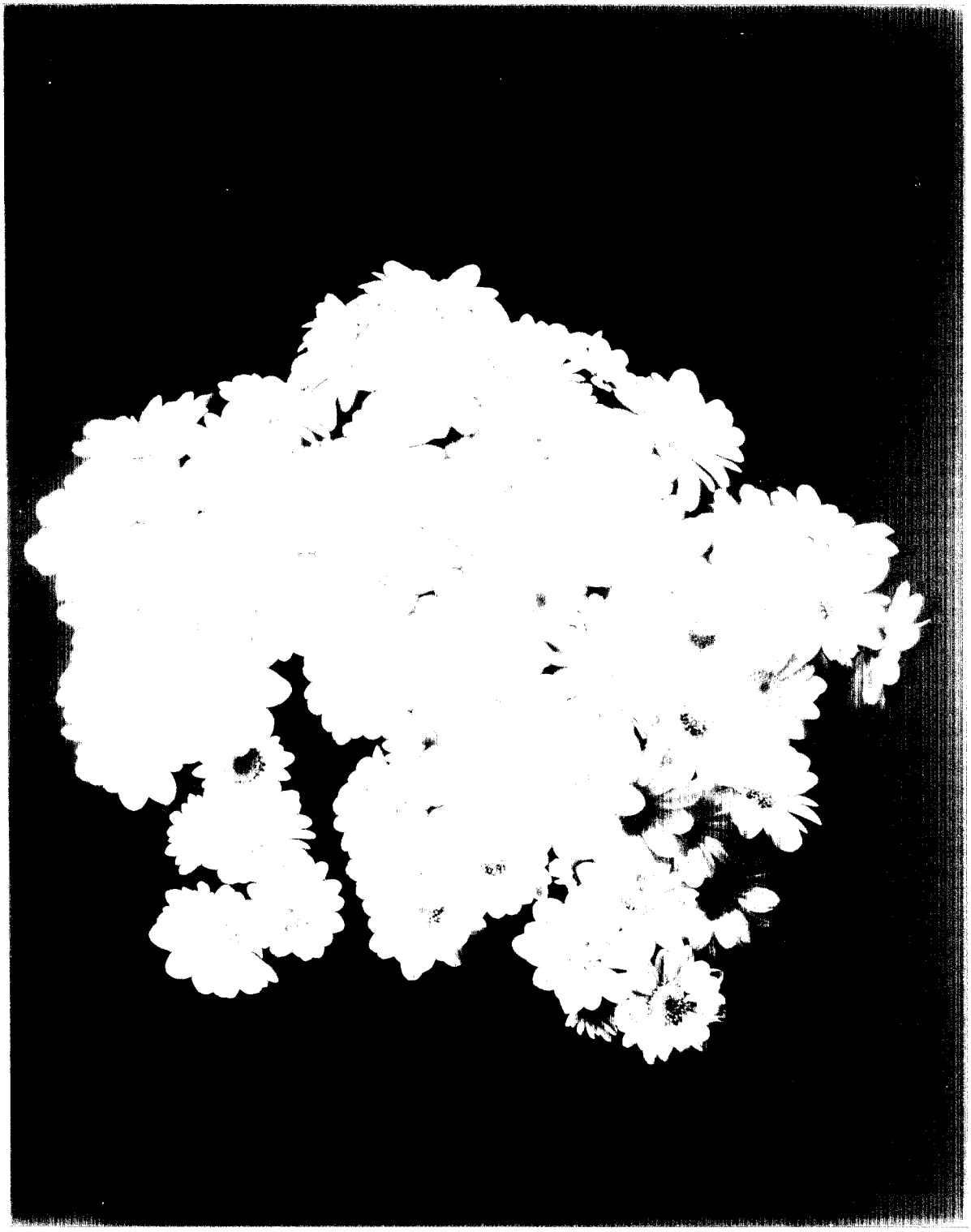

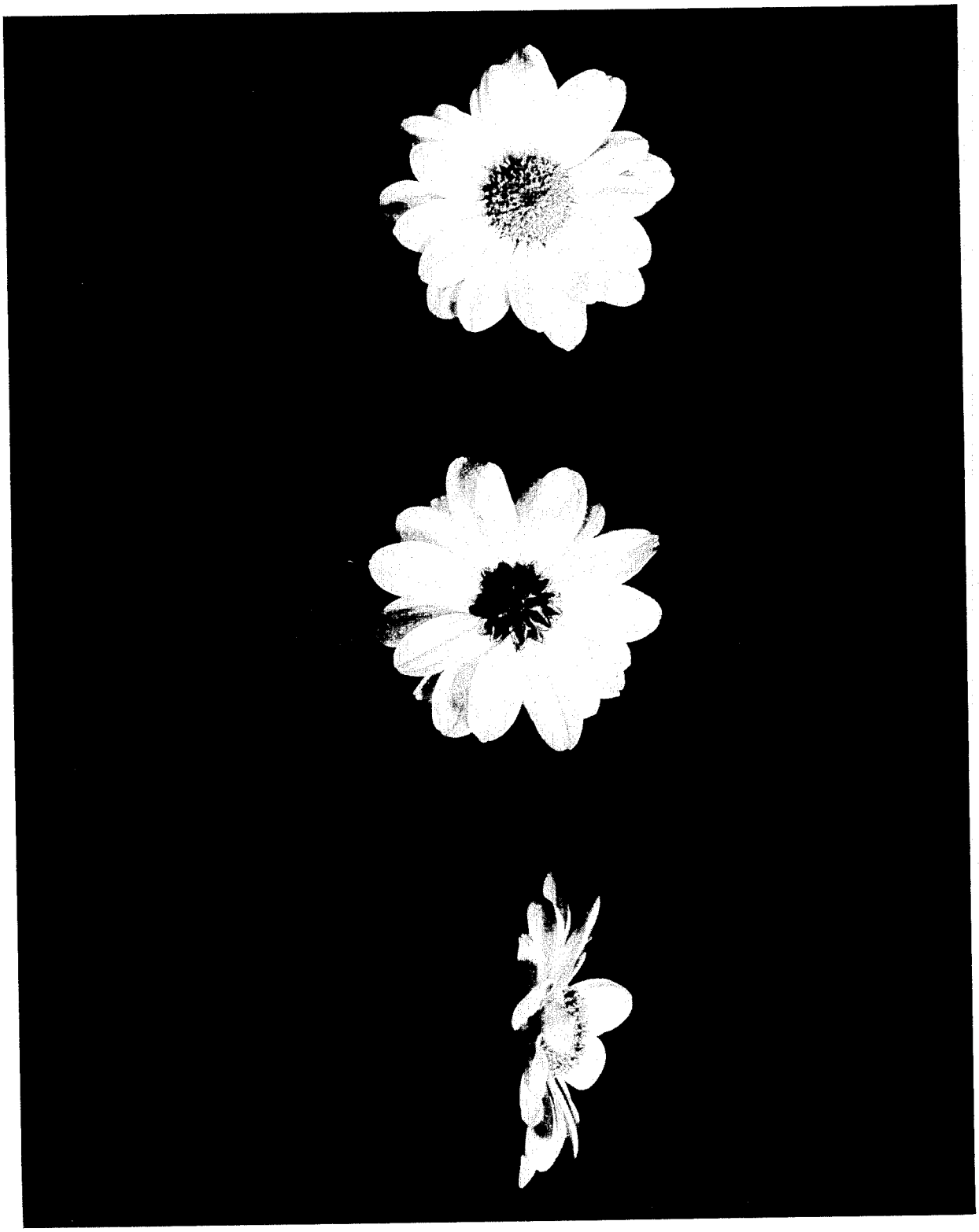

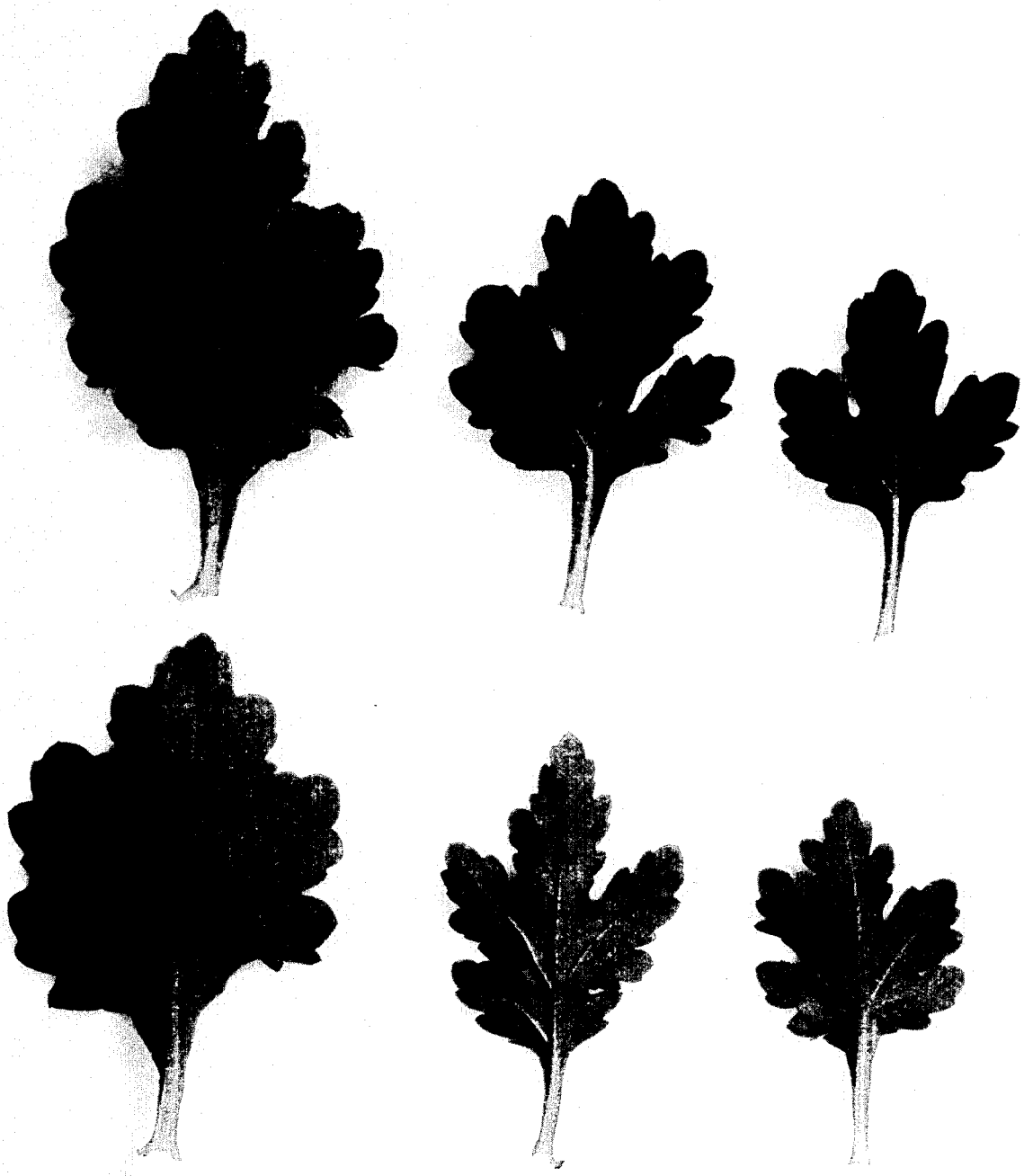

* * * * *